(12) United States Patent
Rabbat et al.

(10) Patent No.: US 11,046,906 B2
(45) Date of Patent: *Jun. 29, 2021

(54) LUBRICANT COMPOSITION

(71) Applicant: BASF SE, Ludwigshafen (DE)

(72) Inventors: Philippe Rabbat, Maplewood, NJ (US); Mary Elizabeth Dery, Putnam Valley, NY (US); Bridgett Rakestraw, Brewster, NY (US); Sai P. Shum, Pleasantville, NY (US); Paul Angelo Odorisio, Leonia, NJ (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,284

(22) Filed: Apr. 23, 2020

(65) Prior Publication Data

US 2020/0248093 A1 Aug. 6, 2020

Related U.S. Application Data

(63) Continuation of application No. 15/756,782, filed as application No. PCT/US2016/050149 on Sep. 2, 2016, now Pat. No. 10,662,390.

(60) Provisional application No. 62/213,241, filed on Sep. 2, 2015.

(51) Int. Cl.
| | | |
|---|---|---|
| *C10M 133/40* | (2006.01) | |
| *C07D 471/04* | (2006.01) | |
| *C10M 169/04* | (2006.01) | |
| *C10N 30/10* | (2006.01) | |
| *C10N 40/25* | (2006.01) | |
| *C10N 40/30* | (2006.01) | |
| *C10N 40/04* | (2006.01) | |
| *C10N 50/10* | (2006.01) | |
| *C10N 40/10* | (2006.01) | |

(52) U.S. Cl.
CPC ......... *C10M 133/40* (2013.01); *C07D 471/04* (2013.01); *C10M 169/04* (2013.01); *C10M 2203/003* (2013.01); *C10M 2203/1025* (2013.01); *C10M 2215/221* (2013.01); *C10M 2215/30* (2013.01); *C10N 2030/10* (2013.01); *C10N 2040/042* (2020.05); *C10N 2040/044* (2020.05); *C10N 2040/10* (2013.01); *C10N 2040/25* (2013.01); *C10N 2040/30* (2013.01); *C10N 2050/10* (2013.01)

(58) Field of Classification Search
CPC .............. C07D 471/04; C10N 2030/10; C10N 2050/10; C10N 2040/30; C10N 2040/25; C10N 2040/044; C10N 2040/042; C10M 133/40; C10M 169/04; C10M 2215/221; C10M 2215/30; C10M 2203/1025; C10M 2203/003

See application file for complete search history.

(56) References Cited

U.S. PATENT DOCUMENTS

| | | | | |
|---|---|---|---|---|
| 5,965,730 A | * | 10/1999 | Ukita | ................... C07D 401/04 544/128 |
| 2003/0191307 A1 | | 10/2003 | Blumenkopf et al. | |
| 2007/0203033 A1 | | 8/2007 | Tynik et al. | |
| 2011/0030269 A1 | * | 2/2011 | Chasan | ............... C10M 133/12 44/388 |
| 2015/0031890 A1 | | 1/2015 | Jeong et al. | |

FOREIGN PATENT DOCUMENTS

| | | |
|---|---|---|
| EP | 0094245 | 11/1983 |
| WO | 2014085284 | 6/2014 |

OTHER PUBLICATIONS

Tae-Gyu Nam et al: "Regioselective Addition of n-Alkyllithiums to [alpha], [alpha]'-Disubstituted-1, 8-Naphthyridines: Synthesis of 6-Amino-3-Pyridinol Analogs of [alpha] -Tocopherol", Systhesis, No. 9, Jan. 1, 2005 (Jan. 1, 2005), pp. 1397-1404, XP055316224, Stuttgart, DE. ISSN: 0039-7881, DOI: 10.1055/s-2005-865308 Scheme 2, 5.

Tae-Gyu Nam et al: "Tetrahydro-1,8-naphthyridinol analogues of [alpha]-tocopherol as antioxidants in lipid membranes and low-density lipoproteins", Journal of the American Chemical Society, vol. 129, No. 33, Aug. 1, 2007 (Aug. 1, 2007), pp. 10211-10219, XP055071907, ISSN: 0002-7863, DOI: 10.1021/ja072371m Scheme 2.

(Continued)

*Primary Examiner* — Vishal V Vasisth

(74) *Attorney, Agent, or Firm* — Lowenstein Sandler LLP

(57) ABSTRACT

A lubricant composition includes a base oil present in an amount of greater than 70 parts by weight per 100 parts by weight of the lubricant composition and an antioxidant. The antioxidant has the structure: wherein each X is independently C-A or N, so long as at least one X is N but no more than two of X are N. Moreover, A is H, cyano or an electron donating group that: (1) has an atom having at least one lone pair of electrons that is bonded directly to the aromatic ring; or (2) is an aryl group or alkyl group. Further, each R is independently H, an alkyl group, or aryl group and each R' is independently an alkyl group or an aryl group.

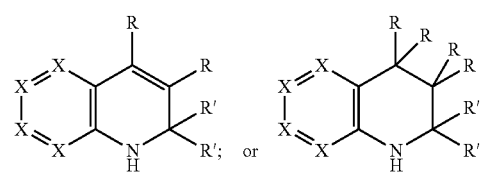

20 Claims, No Drawings

(56) References Cited

OTHER PUBLICATIONS

Paul Messinger et al: "Notiz zur Darstellung partiell hydrierter 5-Hydroxy-1, 7-naphthyridin-Derivate", Liebigs Annalen Der Chemie, vol. 1981, No. 11, Nov. 20, 1981 (Nov. 20, 1981), pp. 2087-2089, XP055039242, ISSN: 0170-2041, DOI: 10.1002/jlac.198119811118 p. 2087.
International Search Report and Written Opinion of the International Searching Authority for PCT/US2016/050140 dated Jan. 20, 2017, 16 pages.

* cited by examiner

LUBRICANT COMPOSITION

CROSS-REFERENCE TO RELATED APPLICATION(S)

This application is a continuation of U.S. patent application Ser. No. 15/756,782 filed on Mar. 1, 2018, now U.S. Pat. No. 10,662,390 dated May 26, 2020, which is a national phase entry of International Application No. PCT/US2016/050149, filed on Sep. 2, 2016, which claims the benefit of U.S. Provisional Patent Application No. 62/213,241, filed on Sep. 2, 2015. The contents of these applications are hereby incorporated by reference in their entirety.

FIELD OF THE DISCLOSURE

This disclosure generally relates to a lubricant composition. More specifically, the lubricant composition includes a particular antioxidant that includes an electron donating group.

BACKGROUND

Lubricant compositions are generally well known in the art and are broadly categorized as oil or water based compositions, i.e., compositions that include large weight percentages of non-polar compounds (such as (base) oils) or large weight percentages of water, respectively. Lubricant compositions are typically further categorized as engine oils, driveline system oils, gear oils, greases, automatic and manual transmission fluids and oils, hydraulic oils, industrial gear oils, turbine oils, rust and oxidation (R&O) inhibited oils, compressor oils, or paper machine oils, etc. Each of these compositions has particular specifications and design requirements and most are designed to minimize corrosion and wear, to resist thermal and physical breakdown, and to be able to minimize the effects of common contaminants such as oxidizing compounds and metal fragments.

Antioxidants are compounds that can retard oxidation, and thus are useful as additives in such lubricant compositions. Antioxidants are commonly utilized in lubricant compositions to assist in reducing unwanted oxidation and increasing performance standards. Combustion engine lubricants oxidize readily at the high operating temperatures of an engine, and in turn, have diminished lubricating capacity as the viscosity of the lubricant increases. Oxidation products also tend to accumulate to form deposits, which in turn leads to greater wear on engine parts. For example, peroxyl radicals can lead to formation of radical chains and ultimately oxidative degradation. Antioxidants are used to react with such radicals, shorten radical chains, and reduce degradation. Unfortunately, many antioxidants do not react as fast as would be desired. Therefore, remains an opportunity for development of improved antioxidants.

SUMMARY OF THE DISCLOSURE

This disclosure provides a lubricant composition that includes a base oil present in an amount of greater than 70 parts by weight per 100 parts by weight of the lubricant composition and also includes an antioxidant. The antioxidant has the structure:

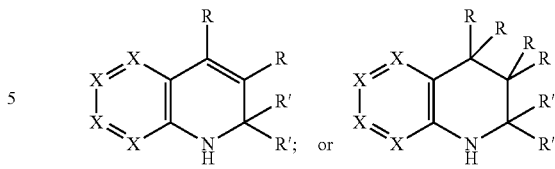

wherein each X is independently C-A or N, so long as at least one X is N but no more than two of X are N. Moreover, A is H, cyano or an electron donating group that: (1) has an atom having at least one lone pair of electrons that is bonded directly to the aromatic ring; or (2) is an aryl group or alkyl group. Further, each R is independently H, an alkyl group, or aryl group and each R' is independently an alkyl group or an aryl group.

DETAILED DESCRIPTION OF THE DISCLOSURE

The present disclosure provides a lubricant composition. In various embodiments, the lubricant composition can be further described as a fully formulated lubricant or alternatively as an engine oil, a driveline system oil, a gear oil, a grease, an automatic and/or manual transmission fluid and/or oil, a hydraulic oil, an industrial gear oil, a turbine oil, a rust and oxidation (R&O) inhibited oil, a compressor oil, a paper machine oil, and/or combinations thereof.

In one embodiment, the terminology "fully formulated lubricant" refers to a total final composition that is a final commercial oil. This final commercial oil may include, for instance, detergents, dispersants, antioxidants, antifoam additives, pour point depressants, viscosity index improvers, anti-wear additives, friction modifiers, and other customary additives, depending on the formulation application. In the art, engine oils may be referred to as including a base oil as described below and performance additives. The lubricant composition of this disclosure includes a base oil and a particular antioxidant and may include any one or more of the aforementioned additives.

Base Oil:

The base oil is not particularly limited and may be further defined as including one or more oils of lubricating viscosity such as natural and synthetic lubricating or base oils and mixtures thereof. In one embodiment, the base oil is further defined as a lubricant. In another embodiment, the base oil is further defined as an oil of lubricating viscosity. In still another embodiment, the base oil is further defined as a crankcase lubricating oil for spark-ignited and compression ignited internal combustion engines, including automobile and truck engines, two-cycle engines, aviation piston engines, and marine and railroad diesel engines. Alternatively, the base oil can be further defined as an oil to be used in gas engines, stationary power engines, and turbines. The base oil may be further defined as a heavy or light duty engine oil. In one embodiment, the base oil is further defined as a heavy duty diesel engine oil. Alternatively, the base oil may be described as an oil of lubricating viscosity or lubricating oil, for instance as disclosed in U.S. Pat. No. 6,787,663 and U.S. 2007/0197407, each of which is expressly incorporated herein by reference in one or more non-limiting embodiments. Alternatively, the base oil may be used in or as an engine oil, driveline system oil, gear oil, grease, automatic and manual transmission fluid or oil, hydraulic oil, industrial gear oil, turbine oil, rust and oxidation (R&O) inhibited oil, compressor oil, or paper machine oil, etc.

The base oil may be further defined as a base stock oil. Alternatively, the base oil may be further defined as a component that is produced by a single manufacturer to the same specifications (independent of feed source or manufacturer's location) that meets the same manufacturer's specification and that is identified by a unique formula, product identification number, or both. The base oil may be manufactured or derived using a variety of different processes including but not limited to distillation, solvent refining, hydrogen processing, oligomerization, esterification, and re-refining. Re-refined stock is typically substantially free from materials introduced through manufacturing, contamination, or previous use. In one embodiment, the base oil is further defined as a base stock slate, as is known in the art.

Alternatively, the base oil may be derived from hydrocracking, hydrogenation, hydrofinishing, refined and re-refined oils or mixtures thereof or may include one or more such oils. In one embodiment, the base oil is further defined as an oil of lubricating viscosity such as a natural or synthetic oil and/or combinations thereof. Natural oils include, but are not limited to, animal oils and vegetable oils (e.g., castor oil, lard oil) as well as liquid petroleum oils and solvent-treated or acid-treated mineral lubricating oils such as paraffinic, naphthenic or mixed paraffinic-naphthenic oils.

In various other embodiments, the base oil may be further defined as an oil derived from coal or shale. Non-limiting examples of suitable oils include hydrocarbon oils such as polymerized and interpolymerized olefins (e.g., polybutylenes, polypropylenes, propylene-isobutylene copolymers, poly(1-hexenes), poly(1-octenes), poly(1-decenes), and mixtures thereof: alkylbenzenes (e.g., dodecylbenzenes, tetradecylbenzenes, dinonylbenzenes, and di(2-ethylhexyl)-benzenes); polyphenyls (e.g., biphenyls, terphenyls, and alkylated polyphenyls), alkylated diphenyl ethers and alkylated diphenyl sulfides and the derivatives, analogs, and homologs thereof.

In still other embodiments, the base oil may be further defined as a synthetic oil which may include one or more alkylene oxide polymers and interpolymers and derivatives thereof wherein terminal hydroxyl groups are modified by esterification, etherification, or similar reactions. Typically, these synthetic oils are prepared through polymerization of ethylene oxide or propylene oxide to form polyoxyalkylene polymers which can be further reacted to form the oils. For example, alkyl and aryl ethers of these polyoxyalkylene polymers (e.g., methylpolyisopropylene glycol ether having a weight average weight average molecular weight of 1.000; diphenyl ether of polyethylene glycol having a weight average molecular weight of 500-1,000; and diethyl ether of polypropylene glycol having a weight average molecular weight of 1.000-1.500) and/or mono- and polycarboxylic esters thereof (e.g. acetic acid esters, mixed $C_3$-$C_8$ fatty acid esters, or the $C_{13}$ oxo acid diester of tetraethylene glycol) may also be utilized.

In even further embodiments, the base oil may include esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, and alkenyl malonic acids) with a variety of alcohols (e.g., butyl alcohol, hexyl alcohol, dodecyl alcohol, 2-ethylhexyl alcohol, ethylene glycol, diethylene glycol monoether, and propylene glycol). Specific examples of these esters include, but are not limited to, dibutyl adipate, di(2-ethylhexyl sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and combinations thereof. Esters useful as the base oil or as included in the base oil also include those formed from $C_5$ to $C_{12}$ monocarboxylic acids and polyols and polyol ethers such as neopentyl glycol, trimethylolpropane, pentaerythritol, dipentaerythritol, and tripentaerythritol.

The base oil may be alternatively described as a refined and/or re-refined oil, or combinations thereof. Unrefined oils are typically obtained from a natural or synthetic source without further purification treatment. For example, a shale oil obtained directly from retorting operations, a petroleum oil obtained directly from distillation, or an ester oil obtained directly from an esterification process and used without further treatment, could all be utilized in this disclosure. Refined oils are similar to the unrefined oils except that they typically have undergone purification to improve one or more properties. Many such purification techniques are known to those of skill in the art such as solvent extraction, acid or base extraction, filtration, percolation, and similar purification techniques. Re-refined oils are also known as reclaimed or reprocessed oils and often are additionally processed by techniques directed to removal of spent additives and oil breakdown products.

The base oil may alternatively be described as specified in the American Petroleum Institute (API) Base Oil Interchangeability Guidelines. In other words, the base oil may be further described as one or a combination of more than one of five base oil groups: Group I (sulfur content >0.03 wt %, and/or <90 wt % saturates, viscosity index 80-120); Group II (sulfur content less than or equal to 0.03 wt %, and greater than or equal to 90 wt % saturates, viscosity index 80-120); Group III (sulfur content less than or equal to 0.03 wt %, and greater than or equal to 90 wt % saturates, viscosity index greater than or equal to 120); Group IV (all polyalphaolefins (PAO's)): and Group V (all others not included in Groups I, II, III, or IV). In one embodiment, the base oil is chosen from API Group I, II, III, IV, V and combinations thereof. In another embodiment, the base oil is chosen from API Group II, III, IV, and combinations thereof. In still another embodiment, the base oil is further defined as an API Group II, III, or IV oil and includes a maximum of about 49.9 wt %, typically up to a maximum of about 40 wt %, more typically up to a maximum of about 30 wt %, even more typically up to a maximum of about 20 wt %, even more typically up to a maximum of about 10 wt % and even more typically up to a maximum of about 5 wt % of the lubricating oil an API Group I or V oil. It is also contemplated that Group II and Group II basestocks prepared by hydrotreatment, hydrofinishing, hydroisomerization or other hydrogenative upgrading processes may be included in the API Group II described above. Moreover, the base oil may include Fisher Tropsch or gas to liquid GTL oils. These are disclosed for example in U.S. 2008/0076687, which is expressly incorporated herein by reference in one or more non-limiting embodiments.

The base oil is typically present in the composition in an amount of from 70 to 99.9, from 80 to 99.9, from 90 to 99.9, from 75 to 95, from 80 to 90, or from 85 to 95, parts by weight per 100 parts by weight of the composition. Alternatively, the base oil may be present in amounts of greater than 70, 75, 80, 85, 90, 91, 92, 93, 94, 95, 96, 97, 98, or 99, parts by weight per 100 parts by weight of the composition. In various embodiments, the amount of lubricating oil in a fully formulated lubricant (including diluent or carrier oils presents) is from about 80 to about 99.5 percent by weight, for example, from about 85 to about 96 percent by weight, for instance from about 90 to about 95 percent by weight. Of course, the weight, percent of the base oil may be any value or range of values, both whole and fractional, within those ranges and values described above and/or may vary from the values and/or range of values above by ±5%, ±10%, ±15%, ±20%, ±25%, ±30%, etc.

Antioxidant:

The lubricant composition also includes an antioxidant. One or more of such antioxidants can be used. The antioxidant has the structure:

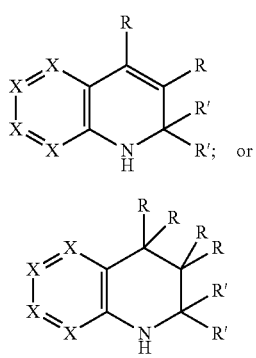

wherein each X is independently C-A or N, i.e., a carbon atom bonded to an "A" group or a nitrogen atom (N), so long as at least one X is N. However, no more than two of X are N. Moreover, A is H (i.e., a hydrogen atom), a cyano group or an electron donating group that: (1) has an atom having at least one lone pair of electrons that is bonded directly to the aromatic ring: or (2) is an aryl group or alkyl group. Further, each R is independently H, an alkyl group, or aryl group and each R' is independently an alkyl group or an aryl group.

In other embodiments, the antioxidant has the structure:

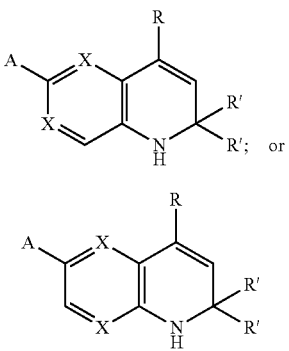

wherein each X is independently CH or N, so long as at least one X is N and wherein A is an electron donating group. The electron donating group (1) has an atom having at least one lone pair of electrons that is bonded directly to the aromatic ring or (2) is an aryl group or alkyl group. Moreover, each R is independently an alkyl group or aryl group which may be any known in the art.

The terminology "aryl" group describes any functional group or substituent derived from an aromatic ring, e.g. phenyl, naphthyl, thienyl, indolyl, etc. The alkyl group may be linear, branched, or cyclic and typically includes 1 to 20 carbon atoms. The alkyl group may include more than 20 carbon atoms. In various embodiments, the alkyl group includes 1, 2, 3, 4, 5, 6, 7, 8, 9, 10, 11, 12, 13, 14, 15, 16, 17, 18, 19, or 20 carbon atoms or any range thereof. The alkyl group may be further defined as an alkane, an alkene, or an alkane. The alkyl group may be alternatively described using the formula $C_nH_{2n+1}$ wherein n is 1 to 20, as described above. In various embodiments, the alkyl group may be described as methyl, ethyl propyl, butyl, t-butyl, pentyl, hexyl, octyl, nonyl, or any isomer thereof.

In various embodiments, the antioxidant has the structure:

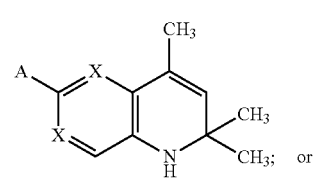

Examples of additional embodiments are as follows:

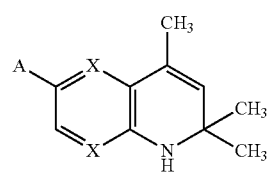

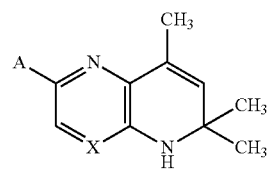

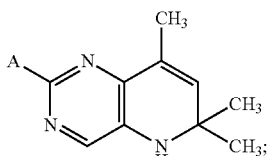

(IX)

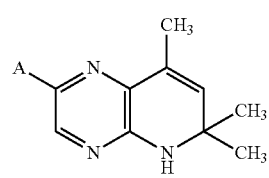

(X)

When one or more carbon atoms within the aromatic ring of the antioxidant is replaced with nitrogen, the resulting compounds may have improved estimated activation enthalpies ($\Delta H^*$) for reactions with peroxyl radicals, while also maintaining a relatively high estimated ionization enthalpy ($\Delta H\langle ion \rangle$) which reflects their stability in air, as compared to the same compounds without the substitution of the nitrogen for carbon. Substitution of nitrogen atoms may produce an increase in the ionization enthalpy ($\Delta H'_{on}$), thus stabilizing the compound to one-electron oxidation (such as by reaction with $O_2$ in air or hydroperoxides arising from hydrocarbon oxidation). This stability may permit substitution with electron-donating groups to increase reactivities as radical-trapping antioxidants by lowering the activation enthalpy ($\Delta H^*$) for reactions with peroxyl radicals.

The electron donating group (1) has an atom having at least one lone pair of electrons that is bonded directly to the aromatic ring of the antioxidant or (2) is an aryl group or alkyl group. The electron donating group can be alternatively described as an "EDG", as is appreciated in the art. In various embodiments, the electron donating group has an atom, such a nitrogen atom, a phosphorous atom, an oxygen atom or a sulfur atom, that has at least one lone pair of electrons. For example, oxygen and sulfur each typically have two lone pairs of electrons while nitrogen and phosphorous each typically have only one lone pair of electrons. The terminology "lone pair" describes a pair of valence electrons that are not shared with other atoms and/or are not used in chemical bonding. These electrons may also be described as a non-bonding pair of electrons. Lone pair electrons are found in the outermost electron shell of atoms. The number of lone pair electrons plus the number of bonding electrons equals the total number of valence electrons around an atom. Examples of atoms having at least one lone pair of electrons that is bonded directly to the aromatic ring of the antioxidant are as follows:

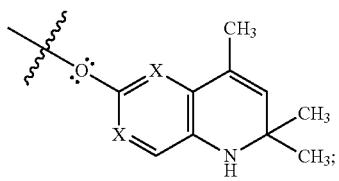

(XI)

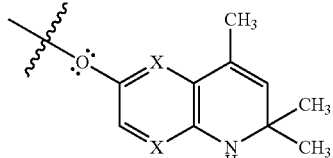

(XII)

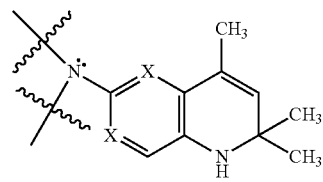

(XIII)

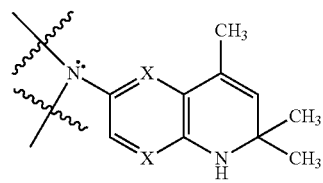

(XIV)

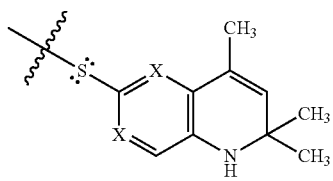

(XV)

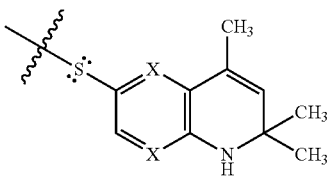

(XVI)

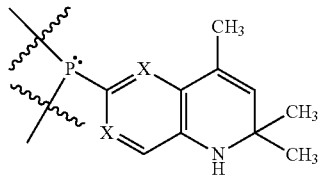

(XVII)

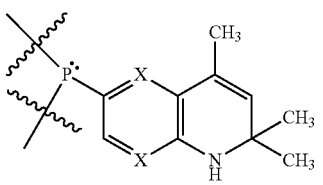

(XVIII)

The electron donating group can alternatively be an aryl group or alkyl group. The terminology "aryl" group describes any functional group or substituent derived from an aromatic ring, e.g. phenyl, naphthyl, thienyl, indolyl, etc. The alkyl group may be linear, branched, or cyclic and typically includes 1 to 20 carbon atoms. Although, the alkyl group may include more than 20 carbon atoms. In various embodiments, the alkyl group includes 1, 2, 3, 4, 5, 6, 7, 8, 9, 10, 11, 12, 13, 14, 15, 16, 17, 18, 19, or 20 carbon atoms or any range thereof. The alkyl group may be further defined as an alkane, an alkene, or an alkane. The alkyl group may be alternatively described using the formula $C_nH_{2n+1}$ wherein n is 1 to 20, as described above. In various embodiments, the alkyl group may be described as methyl, ethyl propyl, butyl, t-butyl, pentyl, hexyl, octyl, nonyl, or any isomer thereof.

In other embodiments, the electron donating group is —NR″$_2$, —NH$_2$, —OH, —OR″, —NHCOR″, or —OCOR″, wherein each R″ is independently an alkyl group having 1 to 10 carbon atoms, as described above. For example, the electron donating group may be —NR″$_2$, wherein each R″ is independently an alkyl group having 1 to 10 carbon atoms, as described above. In another embodiment, the electron donating group is —NH$_2$. In another embodiment, the electron donating group is —OH. In a further embodiment, the electron donating group is —OR″, wherein R″ is an alkyl group having 1 to 10 carbon atoms, as described above. In a further embodiment, the electron donating group is —NHCOR″, wherein R″ is an alkyl group having 1 to 10 carbon atoms, as described above. In another embodiment, the electron donating group is —OCOR″. wherein R″ is an alkyl group having 1 to 10 carbon atoms, as described above. Non-limiting examples of structures corresponding to such embodiments are set forth below:

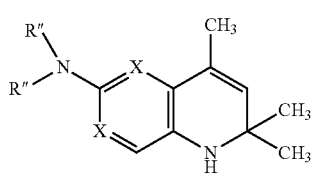
(XIX)

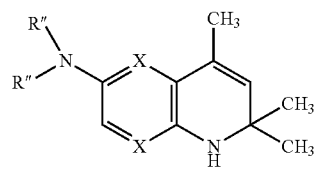
(XX)

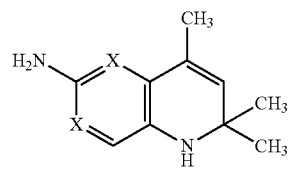
(XXI)

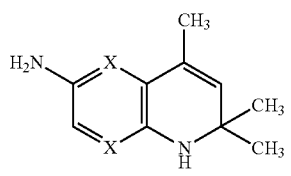
(XXII)

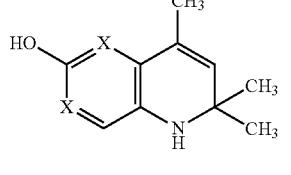
(XXIII)

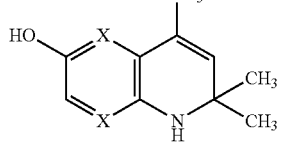
(XXIV)

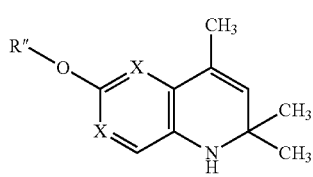
(XXV)

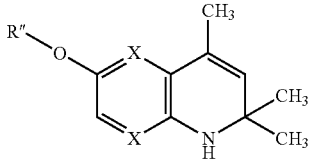
(XXVI)

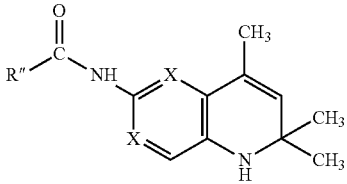
(XXVII)

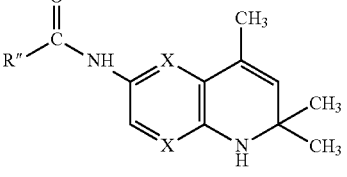
(XXVIII)

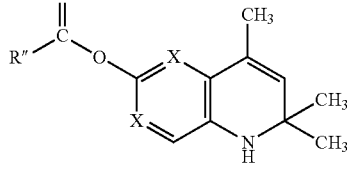
(XXIX)

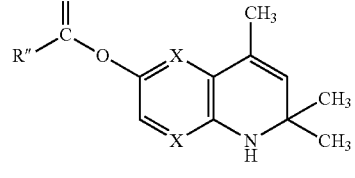
(XXX)

In various non-limiting embodiments, analogs of the each of the aforementioned structures wherein one, two, or three of the methyl groups are each independent R, as described above, are expressly contemplated.

In other embodiments, the electron donating group may be described as aromatic or aliphatic. In still other embodiments, the electron donating group includes or is a hydrocarbon group, an alkoxy group (OR$^3$), an amine group, a monosubstituted amine group (NHR$^3$), or a disubstituted amine group (NR$^3_2$). In other embodiments, the electron donating group may be a diallyl amine. The electron-donating strength of the alkoxy or amine group comes largely from the lone pairs of electrons on the O and N atoms, respectively, such that each of R$^3$ groups can be a hydrogen or a saturated or unsaturated branched or straight chain hydrocarbon moiety and/or may include one or more cycloaliphatic groups and/or one or more aromatic hydrocarbons, or a combination thereof, while not detracting from the electron donating characteristic of the alkoxy or amine group. In such embodiments, the term "cycloaliphatic" describes a saturated or unsaturated carbocyclic moiety comprising mono- or bicyclic rings. Cycloaliphatic groups typically include a 3- to 7-membered saturated carbocyclic moiety. Examples of cycloaliphatic moieties include, but are not limited to, cyclopropyl, cyclobutyl, cyclopentyl, cyclohexyl, cyclohepyl, and the like, including partially unsaturated derivatives thereof such as cyclohexenyl, cyclopentenyl, and the like. Alternatively, the term "hydrocarbon group" may describe a hydrocarbon including from 1 to 20 carbon atoms, e.g. as described above, and includes saturated or unsaturated, branched or straight chain hydrocarbon moieties, including aliphatic moieties and/or one or more cycloaliphatic groups and/or one or more aromatic hydrocarbons, or a combination thereof.

The electron donating group may alternatively be a thiol, sulfide, thioether, or thioester (e.g. wherein the sulfur atom of the group is adjacent to the group being donated into). Alternatively, the electron donating group may be a phosphane.

In still other embodiments, the antioxidant has the following structure:

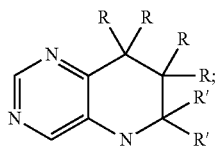
(XXXI)

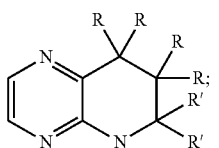
(XXXII)

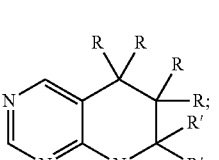
(XXXIII)

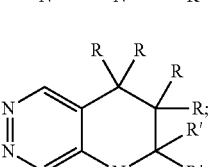
(XXXIV)

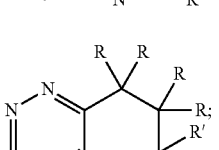
(XXXV)

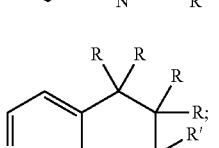
(XXXVI)

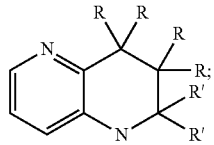
(XXXVII)

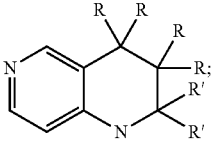
(XXXVIII)

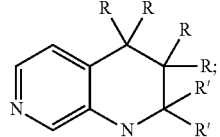
(XXXIX)

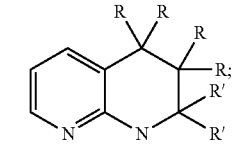
(XL)

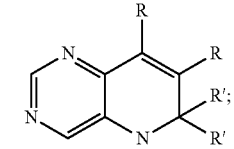
(XLI)

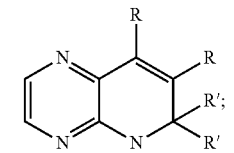
(XLII)

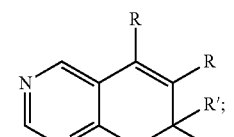
(XLIII)

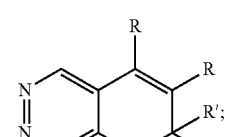
(XLIV)

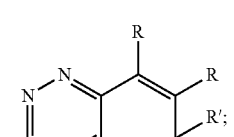
(XLV)

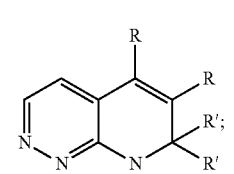
(XLVI)

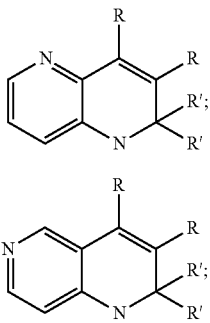

(XLVII)

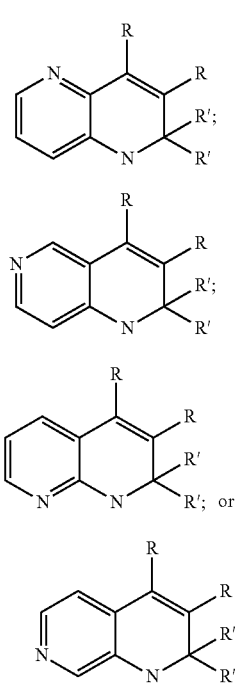

(XLVIII)

(XLIX)

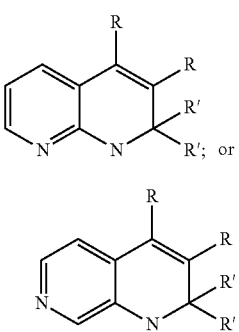

(L)

In addition, combinations of any one or more of the aforementioned antioxidants may be utilized.

The antioxidant is typically present in an amount of, or less than, 30, 25, 20, 15, 10, 5, 2, 1.5, 1, or 0.5, parts by weight per 100 parts by weight of the lubricant composition. In various embodiments, the antioxidant is present in an amount of from of from 0.1 to 2, 0.5 to 2, 1 to 2, or 1.5 to 2, parts by weight per 100 parts by weight of the lubricant composition. Of course, the weight percent of the antioxidant may be any value or range of values, both whole and fractional, within those ranges and values described above and/or may be present in amounts that vary from the values and/or range of values above by ±5%, ±10%, ±15%, ±20%, ±25%, ±30%, etc.

Additives:

The composition can additionally include one or more additives to improve various chemical and/or physical properties. Non-limiting examples of the one or more additives include anti-wear additives, metal passivators, rust inhibitors, viscosity index improvers, pour point depressors, dispersants, detergents, and antifriction additives. One or more of the additives may be ash-including or ash-less.

Anti-Wear Additive:

The anti-wear additive is not particularly limited and may be any known in the art. In one embodiment, the anti-wear additive is selected from the group of ZDDP, zinc dialkyldithio phosphates, and combinations thereof. Alternatively, the anti-wear additive may include sulfur- and/or phosphorus- and/or halogen-including compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thiol propionate, triphenyl thiophosphate (triphenylphosphorothioate), tris(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as N,N-bis(2-ethylhexyl)aminomethyl]-2-mercapto-1H-1,3-benzothiazole, ethoxycarbonyl-5-octyldithiocarbamate, and/or combinations thereof. In one embodiment, the anti-wear additive include phosphorous and sulfur, e.g. in phosphorothionates and/or dithiophosphate esters.

The anti-wear additive is typically present in the composition in an amount of from 0.1 to 20, from 0.5 to 15, from 1 to 10, from 5 to 10, from 5 to 15, from 5 to 20, from 0.1 to 1, from 0.1 to 0.5, or from 0.1 to 1.5, parts by weight per 100 parts by weight of the composition. Alternatively, the anti-wear additive may be present in amounts of less than 20, less than 15, less than 10, less than 5, less than 1, less than 0.5, or less than 0.1, parts by weight per 100 parts by weight of the composition. It is also contemplated that the antiwear additive may be present in an amount of from 0.2 to 0.8, from 0.2 to 0.6, from 0.2 to 0.4, or from 0.3 to 0.5, parts by weight per 100 parts by weight of the composition. Of course, the weight percent of the anti-wear additive may be any value or range of values, both whole and fractional, within those ranges and values described above and/or may vary from the values and or range of values above by ±5%, ±10%, ±15%, ±20%, ±25%, ±30%, etc.

Additional Antioxidants:

The lubricant composition may include one or more additional antioxidants in addition to the antioxidant described above. Suitable, non-limiting, additional antioxidants include alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol 2,6-di-tert-butyl-4-isobutylphenol, 2,6-dicyclopentyl-4-methylphenol, 2-(α-methylcyclohexyl)-4,6-dimethylphenol 2,6-dioctadecyl-4-methylphenol, 2,4,6-tricyclohexylphenol, 2,6-di-tert-butyl-4-methoxymethylphenol, 2,6-di-nonyl-4-methylphenol 2,4-dimethyl-6(1'-methylundec-1'-yl)phenol, 2,4-dimethyl-6-(1'-methylheptadec-1'-yl)phenol, 2,4-dimethyl-6-(1'-methyltridec-1'-yl)phenol, and combinations thereof.

Other non-limiting examples of suitable additional antioxidants includes alkylthiomethyl phenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, and combinations thereof. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate, and combinations thereof, may also be utilized.

Furthermore, hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide, and combinations thereof, may also be used.

It is also contemplated that alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'- methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane, and combinations thereof may be utilized as additional antioxidants.

O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithiol terephthalate, bis(3,5-di-tert-butyl-4-hydroxybenzyl)sulfide, isooctyl-3,5di-tert-butyl-4-hydroxybenzylmercaptoacetate, and combinations thereof, may also be utilized.

Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate, and combinations thereof are also suitable for use as additional antioxidants.

Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate, and combinations thereof, may also be used.

Additional suitable, but non-limiting examples of additional antioxidants include aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, and combinations thereof. Benzylphosphonates, for example dimethyl-2,5-di-tert-butyl-4-hydroxybenzylphosphonate, diethyl-3,5-di-tert-butyl-4-hydroxybenzylphosphonate, dioctadecyl 3,5-di-tert-butyl-4-hydroxybenzylphosphonate, dioctadecyl-5-tert-butyl-4-hydroxy 3-methylbenzylphosphonate, the calcium salt of the monoethyl ester of 3,5-di-tert-butyl-4-hydroxybenzylphosphonic acid, and combinations thereof, may also be utilized. In addition, acylaminophenols, for example 4-hydroxylauranilide, 4-hydroxystearanilide, octyl N-(3,5-di-tert-butyl-4-hydroxyphenyl)carbamate can be used.

Esters of [3-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, and combinations thereof, may also be used. It is further contemplated that esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, and combinations thereof, may be used. Esters of 13-(3,5-dicyclohexyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and combinations thereof, may also be used. Moreover, esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate N,N'-bis(hydroxyethyl)oxamide, 3-thiaundecanol, 3-thiapentadecanol, trimethylhexanediol, trimethylolpropane, 4-hydroxy methyl-1-phospha-2,6,7-trioxabicyclo[2.2.2]octane, and combinations thereof, may be utilized.

Additional non-limiting examples of suitable additional antioxidants include those that include nitrogen, such as amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydropenylpropionyl)hydrazine. Other suitable non-limiting examples of additional antioxidants include aminic antioxidants such as N,N'-diisopropyl-p-phenylenediamine, N,N'-di-sec-butyl-p-phenylenediamine, N,N'-bis(1,4-dimethyl pentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one and 2,2,6,6-tetramethylpiperidin-4-ol, and combinations thereof.

Even further non-limiting examples of suitable additional antioxidants includes aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,1trithiatridecane and 2,2,15,15-tetramethyl-5,12-dihydroxy-3,7,10,14-tetrathiahexadecane, and combinations thereof. Furthermore, sulfurized fatty esters, sulfurized fats and sulfurized olefins, and combinations thereof, may be used.

The one or more additional antioxidants are not particularly limited in amount in the composition but may be present such that a total amount of antioxidants in the composition is about, or less than, 30, 25, 20, 15, 10, 5, 2, 1.5, 1, or 0.5, of from 0.1 to 2, 0.5 to 2, 1 to 2, or 1.5 to 2, parts by weight per 100 parts by weight of the composition. Alternatively, the total amount of antioxidants in the composition may be less than 2, less than 1.5, less than 1, or less than 0.5, parts by weight per 100 parts by weight of the composition. Of course, the weight percent of the one or more additional antioxidants may be any value or range of values, both whole and fractional, within those ranges and values described above and/or may be present in amounts that vary from the values and or range of values above by ±5%, ±10%, ±15%, ±20%, ±25%, ±30%, etc.

Metal Deactivators:

In various embodiments, one or more metal deactivators can be included in the composition. Suitable, non-limiting examples of the one or more metal deactivators include benzotriazoles and derivatives thereof, for example 4- or 5-alkylbenzotriazoles (e.g. triazole) and derivatives thereof, 4,5,6,7-tetrahydrobenzotriazole and 5,5'-methylenebisbenzotriazole; Mannich bases of benzotriazole or triazole, e.g. 1-[bis(2-ethylhexyl)aminomethyl)triazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl) triazole, and combinations thereof.

Additional non-limiting examples of the one or more metal deactivators include 1,2,4-triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles, imidazole derivatives, for example 4,4'-methylenebis(2-undecyl-5-methylimidazole) and bis [(N-methyl)imidazol-2-yl]carbinol octyl ether, and combinations thereof.

Further non-limiting examples of the one or more metal deactivators include sulfur-including heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one, and combinations thereof. Even further non-limiting examples of the one or more metal deactivators include amino compounds, for example salicylidenepropylenediamine, salicylaminoguanidine and salts thereof, and combinations thereof.

The one or more metal deactivators are not particularly limited in amount in the composition but are typically present in an amount of from 0.01 to 0.1, from 0.05 to 0.01, or from 0.07 to 0.1, parts by weight per 100 parts by weight of the composition. Alternatively, the one or more metal deactivators may be present in amounts of less than 0.1, of less than 0.7, or less than 0.5, parts by weight per 100 parts by weight of the composition. The weight percent of the one or more metal deactivators may be any value or range of values, both whole and fractional, within those ranges and values described above and/or may be present in amounts that vary from the values and/or range of values above by ±5%, ±10%, ±15%, ±20%, ±25%, ±30%, etc.

Rust Inhibitors and Friction Modifiers:

In various embodiments, one or more additional rust inhibitors and/or one or more friction modifiers can be included in the composition. Suitable, non-limiting examples of the one or more additional rust inhibitors and/or one or more friction modifiers include organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof, and combinations thereof. Additional suitable, non-limiting examples of the one or more rust inhibitors and/or friction modifiers include nitrogen-including compounds, for example, primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol, and combinations thereof. Further suitable, non-limiting examples include heterocyclic compounds, for example: substituted imidazolines and oxazolines, and 2-heptadecenyl-1-(2-hydroxyethyl)imidazoline, phosphorus-including compounds, for example: Amine salts of phosphoric acid partial esters or phosphonic acid partial esters, and zinc dialkyldithiophosphates, molybdenum-including compounds, such as molybdenum dithiocarbamate and other sulfur and phosphorus including derivatives, sulfur-including compounds, for example: barium dinonylnaphthalenesulfonates, calcium petroleum sulfonates, alkylthio-substituted aliphatic carboxylic acids, esters of aliphatic 2-sulfocarboxylic acids and salts thereof, glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols, and combinations thereof.

The one or more additional rust inhibitors and/or one or more friction modifiers are not particularly limited in amount in the composition but may be present in an amount of from 0.05 to 0.5, 0.01 to 0.2, from 0.05 to 0.2, 0.1 to 0.2, 0.15 to 0.2, or 0.02 to 0.2, parts by weight per 100 parts by weight of the composition. Alternatively, the one or more additional rust inhibitors and/or one or more friction modifiers may be present in amounts of less than 0.5, less than 0.4, less than 0.3, less than 0.2, less than 0.1, less than 0.5, or less than 0.1, parts by weight per 100 parts by weight of the composition. The weight percent of the one or more rust inhibitors and friction modifiers may be any value or range of values, both whole and fractional, within those ranges and values described above and/or may be present in amounts that vary from the values and/or range of values above by ±5%, ±10%, ±15%, ±20%, ±25%, ±30%, etc.

Viscosity Index Improvers:

In various embodiments, one or more viscosity index improvers can be included in the composition. Suitable, non-limiting examples of the one or more viscosity index improvers include polyacrylates, polymethacrylates, vinylpyrrolidone/methacrylate copolymers, polyvinylpyrrolidones, polybutenes, olefin copolymers, styrene/acrylate copolymers and polyethers, and combinations thereof. The one or more viscosity index improvers are not particularly limited in amount in the composition but are typically present in an amount of from 1 to 1, from 2 to 8, from 3 to 7, from 4 to 6, or from 4 to 5, parts by weight per 100 parts by weight of the composition. Alternatively, the one or more viscosity index improvers may be present in an amount of less than 10, 9, 8, 7, 6, 5, 4, 3, 2, or 1, part by weight per 100 parts b eight of the composition. The weight percent of the one or more viscosity index improvers may be any value or range of values, both whole and fractional, within those ranges and values described above and/or may be present in amounts that vary from the values and/or range of values above by ±5%, ±10%, ±15%, ±20%, ±25%, ±30%, etc.

Pour Point Depressants:

In various embodiments, one or more pour point depressants can be included in the composition. Suitable, non-limiting examples of the pour point depressants include polymethacrylate and alkylated naphthalene derivatives, and combinations thereof. The one or more pour point depressants are not particularly limited in amount in the composition but are typically present in an amount of from 0.1 to 1, from 0.5 to 1, or from 0.7 to 1, part by weight per 100 parts by weight of the composition. Alternatively, the one or more pour point depressants may be present in amounts of less than 1, less than 0.7, or less than 0.5, parts by weight per 100 parts by weight of the composition. The weight percent of the one or more pour point depressants may be any value or range of values, both whole and fractional, within those ranges and values described above and/or may be present in amounts that vary from the values and/or range of values above by ±5%, ±10%, ±15%, ±20%, ±25%, ±30%, etc.

Dispersants:

In various embodiments, one or more dispersants can be included in the composition. Suitable, non-limiting examples of the one or more dispersants include polybutenylsuccinic amides or -imides, polybutenylphosphonic acid derivatives and basic magnesium, calcium and barium sulfonates and phenolates, succinate esters and alkylphenol amines (Mannich bases), and combinations thereof.

The one or more dispersants are not particularly limited in amount in the composition but are typically present in an amount of from 0.1 to 5, from 0.5 to 4.5, from 1 to 4, from 1.5 to 3.5, from 2 to 3, or from 2.5 to 3, parts by weight per 100 parts by weight of the composition. Alternatively, the one or more dispersants may be present in an amount of less than 5, 4.5, 3.5, 3, 2.5, 2, 1.5, or 1, part by weight per 100 parts by weight of the composition. The weight percent of the one or more dispersants may be any value or range of values, both whole and fractional, within those ranges and values described above and/or may be present in amounts that vary from the values and/or range of values above by ±5%, ±10%, ±15%, ±20%, ±25%, ±30%, etc.

Detergents:

In various embodiments, one or more detergents can be included in the composition. Suitable, non-limiting examples of the one or more detergents include overbased or neutral metal sulphonates, phenates and salicylates, and combinations thereof.

The one or more detergents are not particularly limited in amount in the composition but are typically present in an amount of from 0.1 to 5, from 0.5 to 4.5, from 1 to 4, from 1.5 to 3.5, from 2 to 3, or from 2.5 to 3, parts by weight per 100 parts by weight of the composition. Alternatively, the one or more detergents may be present in an amount of less than 5, 4.5, 3.5, 3, 2.5, 2, 1.5, or 1, part by weight per 100 parts by weight of the composition. The weight percent of the one or more detergents may be any value or range of values, both whole and fractional, within those ranges and values described above and/or may be present in amounts that vary from the values and/or range of values above by ±5%, ±10%, ±15%, ±20%, ±25%, ±30%, etc.

In various embodiments, the composition is substantially free of water, e.g. includes less than 5, 4, 3, 2, or 1, weight percent of water. Alternatively, the composition may include less than 0.5 or 0.1 weight percent of water, less than 500, 100, 50, 20, 15, 10, or 5, parts by weight of water per one million parts by weight (ppm) of the composition, or may be free of water. Of course, the weight percent of the water may be any value or range of values, both whole and fractional, within those ranges and values described above and/or may be present in amounts that vary from the values and/or range of values above by ±5%, ±10%, ±15%, ±20%, ±25%, ±30%, etc.

The lubricant composition may be further defined as ash-including or ash-less, according to ASTM D 874 and known in the art. Typically, the terminology "ash-less" refers to the absence of (significant) amounts of metals such as sodium, potassium, calcium, and the like. Of course, it is to be understood that the lubricant composition is not particularly limited to being defined as either ash-including or ash-less.

Additive Concentrate Package:

The instant disclosure also provides an additive concentrate package which includes the antioxidant of this disclosure and also includes one or more metal deactivators, one or more anti-wear additives, one or more additional antioxidants, and/or one or more of the aforementioned additives. The additive concentrate package may include the antioxidant of this disclosure and be free of any additional antioxidants. In one embodiment, the additive concentrate package is further defined as a hydraulic additive concentrate package. In another embodiment, the additive concentrate package is further defined as an engine oil additive concentrate package. In a further embodiment, the additive concentrate package is further defined as a driveline system oil additive concentrate package. In an additional embodiment, the additive concentrate package is further defined as a gear oil additive concentrate package. In still another embodiment, the additive concentrate package is further defined as a grease additive concentrate package. In a further embodiment, the additive concentrate package is further defined as an automatic and/or manual transmission fluid and/or oil additive concentrate package. In another embodiment, the additive concentrate package is further defined as an industrial gear oil additive concentrate package. In another embodiment, the additive concentrate package is further defined as a turbine oil additive concentrate package. In another embodiment, the additive concentrate package is further defined as a rust and oxidation inhibited oil additive concentrate package. In another embodiment, the additive concentrate package is further defined as a compressor oil additive concentrate package. In another embodiment, the additive concentrate package is further defined as a paper machine oil additive concentrate package. In another embodiment, the additive concentrate package is further defined as an additive concentrate package for combinations of two or more of the aforementioned oils.

In another embodiment, the additive concentrate package includes 10-40 weight percent of the antioxidant, 0-15 weight percent of a metal deactivator (e.g. a yellow metal corrosion inhibitor), 0-15 weight percent of a corrosion inhibitor (e.g. the corrosion inhibitor of this disclosure and a ferrous metal corrosion inhibitor), 0-10 weight percent of a friction modifier (e.g. glycerol mono-oleate), 20-35 weight percent of an anti-wear additive, and 0-1 weight percent of an anti-foam additive. Additionally, 0-25 weight percent of a dispersant may also be included. Viscosity modifiers and pour point depressants may also be included but typically are not part of such packages.

Some of the compounds described above may interact in the lubricant composition, so the components of the lubricant composition in final form may be different from those components that are initially added or combined together. Some products formed thereby, including products formed upon employing the composition of this disclosure in its intended use, are not easily described or describable. Nevertheless, all such modifications, reaction products, and products formed upon employing the composition of this disclosure in its intended use, are expressly contemplated and hereby included herein in various non-limiting embodiments. Various embodiments of this disclosure include one or more of the modification, reaction products, and products formed from employing the composition, as described above.

Method of Forming the Composition:

This disclosure also provides a method of forming the composition. The method includes the steps of providing the base oil, providing the antioxidant of this disclosure and combining the base oil and the antioxidant. The method may also include one or more steps of providing any one or more of the aforementioned additives and combining the one or more aforementioned additives with the base oil and/or antioxidant of this disclosure in any order and in any amounts.

Antioxidant Independent from Composition:

This disclosure also provides the antioxidant itself independent from any lubricant composition. The antioxidant may be any as described herein.

Method of Making the Antioxidant:

This disclosure also provides a method of making the antioxidant. In various embodiments, the method includes the steps of providing an amino dialkylaminopyrimidine wherein the alkyl groups each independently have from 1 to 20 carbon atoms, providing a catalytic amount of iodine, providing acetone, and combining the amino dialkylaminopyrimidine, the iodine, and the acetone to form the antioxidant of this disclosure.

In other embodiments, the method may include one or more steps as outline below. One of skill in the art may change the starting materials as needed. For example, any suitable second amine may be utilized in place of the bis-2-ethylhexylamine. In still other embodiments, the method includes one or more steps as described in EP 94245, which is expressly incorporated herein in its entirety in various non-limiting embodiments. For example, one of skill in the art may select one or more synthetic steps from EP 94245 to form the antioxidant of the instant disclosure.

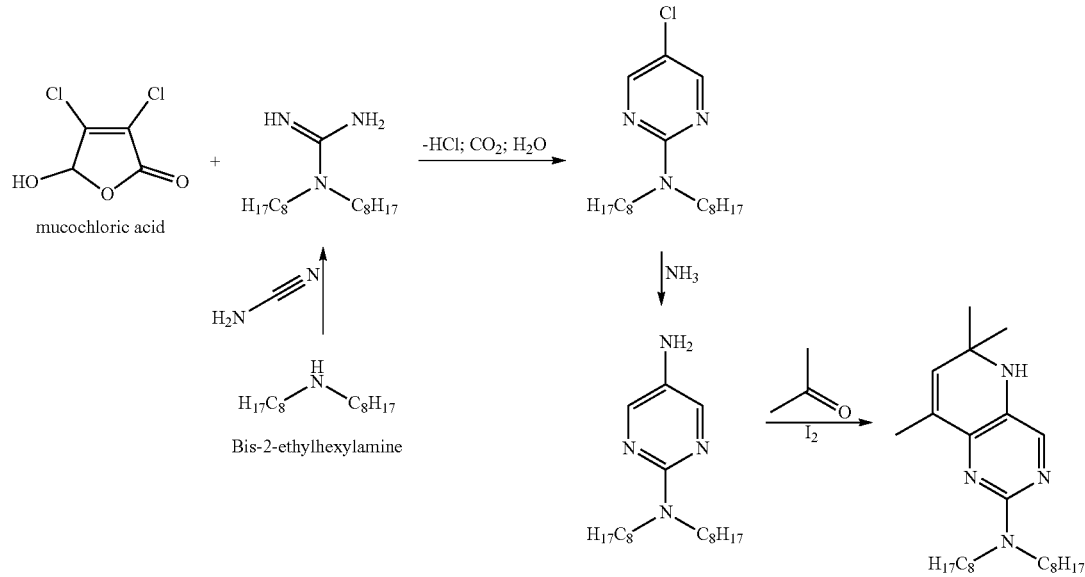

The alkyl groups of the dialkylaminopyrimidine may each independently be linear, branched, or cyclic and typically includes 1 to 20 carbon atoms. The alkyl group may include more than 20 carbon atoms. In various embodiments, the alkyl group includes 1, 2, 3, 4, 5, 6, 7, 8, 9, 10, 11, 12, 13, 14, 15, 16, 17, 18, 19, or 20 carbon atoms or any range thereof. The alkyl group may be further defined as an alkane, an alkene, or an alkyne. The alkyl group may be alternatively described using the formula $C_nH_{2n+1}$ wherein n is 1 to 20, as described above. In various embodiments, the alkyl group may be described as methyl, ethyl propyl, butyl, t-butyl, pentyl, hexyl, octyl, nonyl, or any isomer thereof.

In various non-limiting embodiments, one or more of the antioxidants of the instant disclosure may be utilized in combination with one or more antioxidants described in provisional application Ser. No. 62/213,245, provisional application Ser. No. 62/213,241, provisional application Ser. No. 62/213,239, provisional application Ser. No. 62/347,907, U.S. national stage application Ser. No. 15/756,782, which is a national stage entry of PCT application number PCT/US16/050149, and/or U.S. national stage application Ser. No. 15/756,848, which is a national stage entry of PCT application number PCT/US16/050140, each of which U.S. application is expressly incorporated herein by reference in its entirety in various non-limiting embodiments.

EXAMPLES

An example of the antioxidant of this disclosure can be formed as follows:

Example 1

In a dry flask 5-amino-N,N-dioctylaminopyrimidine and a catalytic amount of iodine are mixed with acetone as a solvent. The resultant reaction mixture is heated until complete. Upon completion of the reaction, the mixture is cooled and the product is isolated.

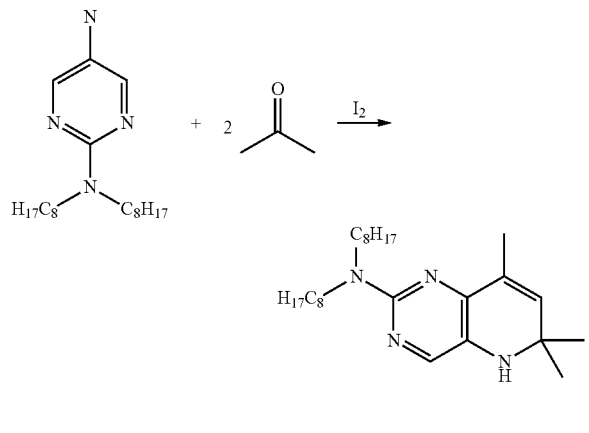

Example 2

1,2-dihydro-6-methoxy-2,2,4-trimethyl-1,5-naphthyridine: In a 1 L 3 neck round bottom flask equipped with a reflux condenser connected to a nitrogen gas source, a thermocouple, and a magnetic stir bar was dissolved 52.48 g of 5-amino-2-methoxypyridine in 500 mL of acetone. To the resultant solution was added 6.8 g of iodine. The resultant mixture was stirred under a nitrogen atmosphere and heated at reflux, internal measured reaction temperature was 60° C. After 14 hr of heating the resultant mixture was cooled to ambient temperature and concentrated under vacuum to give a dark viscous crude oil. The crude reaction mixture was dissolved into dichloromethane and passed through a short column of silica gel eluting with dichloromethane to afford 69 g (80% yield) of 1,2-dihydro-6-methoxy-2,2,4-trimethyl-1,5-naphthyridine as a yellow oil. $^1$H NMR (500 MHz, CDCl$_3$): δ 1.26 (s, 6H), 2.05 (s, 3H), 3.4 (s, 1H), 3.86 (s, 3H), 5.49 (s, 1H), 6.4 (d, 1H), 6.7 (d, 1H). This reaction is also set forth visually below:

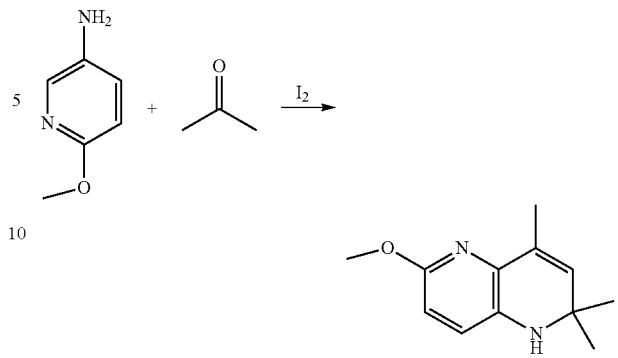

Example 3

6-methoxy-1,2,3,4-tetrahydro-2,2,4-trimethyl-1,5-naphthyridine: In a 600 mL pressure bottle equipped with a magnetic stir bar was dissolved 10 g of 1,2-dihydro-6-methoxy-2,2,4-trimethyl-1,5-naphthyridine in 30 mL of ethanol. To the resultant solution was added 0.75 g of 10% Pd on carbon as a catalyst using an additional 25 mL of ethanol to ensure complete transfer of the catalyst to the flask. The resultant mixture was purged with nitrogen and was reacted under a hydrogen pressure of 20 to 40 psi until no further hydrogen was absorbed. The reaction mixture was purged with nitrogen and the catalyst removed by filtration. The filtrate was concentrated under vacuum to afford 9.93 g (98% yield) of 6-methoxy-1,2,3,4-tetrahydro-2,2,4-trimethyl-1,5-naphthyridine as a light amber oil. $^1$H NMR (500 MHz, CDCl$_3$): δ 1.17 (s, 3H), 1.24 (s, 3H), 1.39 (d, 3H), 1.5 (t, 1H), 1.84 (dd, 1H), 2.93 (m, 1H), 3.05 (s, 1H), 3.87 (s, 3H), 6.41 (d, 1H), 6.76 (d, 1H), MS: m/z=207 (M)'. This reaction is also set forth visually below:

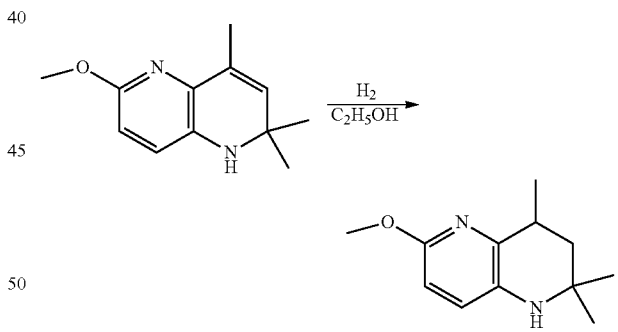

After formation, the antioxidant formed in Example 3 is added to an oil which is evaluated to determine Oxidation Induction Time using High Pressure Differential Scanning calorimetry and ASTM D6186. Various comparative compositions are also formed that include none of the antioxidant. The results are set forth immediately below.

| | Oxidation Induction Time – mins |
|---|---|
| Composition 1 | 16 |
| 0.5 wt % Antioxidant of Example 3; HDDEO-Group III* | |

-continued

| | Oxidation Induction Time – mins |
|---|---|
| Composition 2 | 20 |
| 1.5 wt % Antioxidant of Example 3; HDDEO-Group III* | |
| Composition 3 | 27 |
| 2 wt % Antioxidant of Example 3; HDDEO-Group II* | |
| Composition 4 | 8 |
| 2 wt % Antioxidant of Example 3; EHC 45** | |
| Comparative Compositions 1 and 2 | 7 |
| HDDEO-Group III; No Antioxidant* | |
| Comparative Composition 3 | 4 |
| HDDEO-Group II; No Antioxidant* | |
| Comparative Composition 4 | 3 |
| EHC 45; No Antioxidant** | |

*Run at 200° C.; 500 psi;
**Run at 200° C.; 150 psi

Based on the data shown in the Table above, use of the antioxidants shows improved Oxidation Induction Time for compositions including 0.5-2 wt % antioxidant compared to the Comparative Compositions without antioxidant present.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A method of forming a lubricant composition, comprising:
    combining a base oil and an antioxidant to form the lubricant composition,
    wherein the antioxidant comprises the structure:

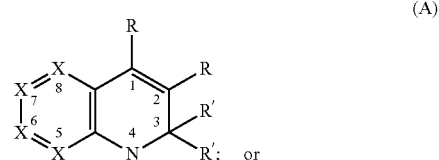

(A)

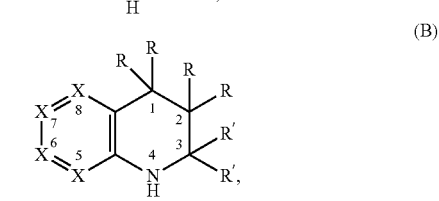

(B)

wherein each X is independently C-A or N, so long as at least one X is N but no more than two of X are N; and
    wherein A is H, cyano or an electron donating group that:
        (1) has an atom having at least one lone pair of electrons that is bonded directly to the aromatic ring; or
        (2) is an aryl group or alkyl group; and
    wherein each R is independently H, an alkyl group, or aryl group and each R' is independently an alkyl group or an aryl group,
    with the proviso that in structure (A) when the X in the 8 position is N, at least one of the following substitutions is present: (i) at least one A is not H, (ii) another X is N, or (iii) the R attached to the carbon in the 2 position is not H.

2. The method of claim 1, further comprising:
    forming the antioxidant, comprising:
        combining an amino dialkylaminopyrimidine, a catalytic amount of iodine and acetone to form the antioxidant,
        wherein the alkyl groups of the dialkylaminopyrimidine each independently comprise from 1 to 20 carbon atoms.

3. The method of claim 2, wherein the alkyl groups of the dialkylaminopyrimidine is each independently linear, branched or cyclic.

4. The method of claim 2, wherein the alkyl groups of the dialkylaminopyrimidine is each independently an alkane, an alkene or an alkyne.

5. The method of claim 2, wherein the alkyl groups of the dialkylaminopyrimidine is each independently a methyl, ethyl, propyl, butyl, t-butyl, pentyl, hexyl, octyl, nonyl or an isomer thereof.

6. The method of claim 2, wherein the alkyl groups of the dialkylaminopyrimidine each independently comprises the formula $C_nH_{2n+1}$, wherein n is an integer from 1 to 20.

7. The method of claim 1, wherein the base oil is present in an amount of greater than 70 parts by weight per 100 parts by weight of the lubricant composition.

8. The method of claim 1, wherein the base oil comprises at least one of an API Group I, Group II and Group III oil.

9. The method of claim 1, wherein the base oil comprises at least one of a mineral oil and a synthetic base oil.

10. The method of claim 1, wherein said antioxidant comprises the structure:

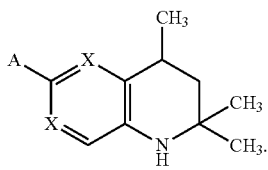

11. The method of claim 1, wherein said antioxidant comprises the structure:

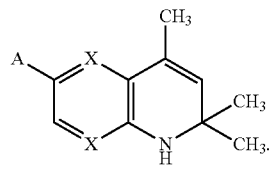

12. The method of claim 1, wherein A is an electron donating group that has an oxygen atom or nitrogen atom that is bonded directly to the aromatic ring.

13. The method of claim 1, wherein said electron donating group is $NR''_2$, —$NH_2$, —OH, —OR", —NHCOR", or OCOR", wherein each R" is independently an alkyl group having 1 to 10 carbon atoms.

14. The method of claim 1, wherein said electron donating group is $NR''_2$, —OR", —NHCOR" or —OCOR", wherein each R" is an alkyl group having 1 to 10 carbon atoms.

15. The method of claim 1, wherein said electron donating group is an alkyl group having 1 to 20 carbon atoms.

16. The method of claim 1, wherein said electron donating group is an aryl group.

17. The method of claim 1, wherein two of X are N.

18. The method of claim 1, wherein said antioxidant is present in an amount of from 0.1 to 2 parts by weight per 100 parts by weight of said lubricant composition.

19. The method of claim 1, further comprising combining the base oil and the antioxidant with one or more additive.

20. The method of claim 19, wherein the one or more additive comprises at least one of a detergent, a dispersant, an antifoam agent, an additional antioxidant, a pour point depressant, a viscosity index improver, an anti-wear agent and a friction modifier.

\* \* \* \* \*